(12) United States Patent
Christoforidis et al.

(10) Patent No.: US 9,833,523 B2
(45) Date of Patent: Dec. 5, 2017

(54) PHARMACOKINETIC DETERMINATION OF INTRAVITREAL AGENTS

(71) Applicant: The Ohio State University, Columbus, OH (US)

(72) Inventors: John B. Christoforidis, Columbus, OH (US); Michael V. Knopp, Columbus, OH (US)

(73) Assignee: The Ohio State University, Columbus, OH (US)

( * ) Notice: Subject to any disclaimer, the term of this patent is extended or adjusted under 35 U.S.C. 154(b) by 272 days.

(21) Appl. No.: 13/868,453

(22) Filed: Apr. 23, 2013

(65) Prior Publication Data

US 2013/0295006 A1 Nov. 7, 2013

Related U.S. Application Data

(60) Provisional application No. 61/637,318, filed on Apr. 24, 2012.

(51) Int. Cl.
*A61K 51/00* (2006.01)
*A61M 36/14* (2006.01)
*A61K 51/10* (2006.01)

(52) U.S. Cl.
CPC ........ *A61K 51/1021* (2013.01); *A61K 51/109* (2013.01); *A61K 51/1084* (2013.01)

(58) Field of Classification Search
CPC ................ A61K 49/00; A61K 49/0004; A61K 49/0008; A61K 38/00; A61K 49/0419; A61K 49/0433; A61K 49/0442; A61K 49/0461; A61K 2123/00; A61K 2121/00; A61K 51/10; A61K 2039/505; A61K 51/088; A61K 51/0497; A61K 51/1021; A61K 51/109; A61K 51/51; A61K 51/1084; A01K 2217/05; G01N 33/5088
USPC .......... 424/1.11, 1.49, 1.65, 1.81, 1.85, 1.89, 424/9.1, 9.4, 9.2
See application file for complete search history.

(56) References Cited

U.S. PATENT DOCUMENTS

| | | | |
|---|---|---|---|
| 5,543,293 A | 8/1996 | Gold et al. | |
| 5,579,250 A | 11/1996 | Balaji et al. | |
| 5,580,737 A | 12/1996 | Polisky et al. | |
| 5,612,895 A | 3/1997 | Balaji et al. | |
| 5,631,146 A | 5/1997 | Szostak et al. | |
| 5,631,280 A | 5/1997 | Ciccarone et al. | |
| 5,786,462 A | 7/1998 | Schneider et al. | |
| 2012/0276192 A1 | 11/2012 | Reich et al. | |
| 2012/0308645 A1 | 12/2012 | Reich et al. | |

OTHER PUBLICATIONS

Christoforidis et al, Invest. Ophthalmol. Vis. Sci., 2011, vol. 52, pp. 5899-5903.*
Wu et al, Seminars in Ophthalmology, 2009, vol. 24, pp. 100-105.*
John, Kerala Journal of Ophthalmology, 2007, vol. XIX, No. 1, pp. 46-57.*
Brown et al., Ranibizumab versus Verteporfin for Neovascular Age-Related Macular Degeneration, N. Engl. J. Med., (2006) 355:1432-1444.
Christoforidis et al., PET/CT Imaging of I-124-Radiolabeled Bevacizumab and Ranibizumab after Intravitreal Injection in a Rabbit Model, Invest. Ophthalmol. Vis. Sci., 52:5899-5903 (2011).
Cortez et al., Intravitreous Bevacizumab Injection, Arch. Ophthalmol., 129:884-887 (2010).
Gaudreault et al., Preclinical Pharmacokinetics of Ranibizumab (rhuFabV2) after a Single Intravitreal Administration, Invest Ophthalmol. Vis. Sci., 46(2):726-733 (2005).
Gisladottir et al., Diffusion characteristics of vitreous humour and saline solution follow the Stokes Einstein equation, Graefes. Arch. Clin. Exp. Ophthalmol., 247(12):1677-1684 (2009).
Goldenberg et al., Posterior Vitreous Detachment With Microplasmin Alters the Retinal Penetration of Intravitreal Bevacizumab (Avastin) in Rabbit Eyes, Retina, 31(2):393-400 (2011).
Klettner et al., Comparison of Bevacizumab, Ranibizumab, and Pegaptanib In Vitro: Efficiency and Possible Additional Pathways, Invest. Ophthalmol. Vis. Sci., 49(10):4523-4527 (2008).
Papadopoulos et al., Binding and neutralization of vascular endothelial growth factor (VEGF) and related ligands by VEGF Trap, ranibizumab and bevacizumab, Angiogenesis, 15:171-185 (2012).
Rosenfeld et al., Ranibizumab for Neovascular Age-Related Macular Degeneration, N. Engl. J. Med., 355(14):1419-1431 (2006).
Shah et al., Thromboembolic Events in Gastric Cancer: High Incidence in Patients Receiving Irinotecan- and Bevacizumab-Based Therapy, J. Clin. Oncol., 23(11):2574-2576 (2005).
Yang et al., A Randomized Trial of Bevacizumab, an Anti—Vascular Endothelial Growth Factor Antibody, for Metastatic Renal Cancer, N. Engl. J. Med., 349(5):427-434 (2003).
Zou et al., 124I-HuCC49deltaCH2 for TAG-72 antigen-directed positron emission tomography (PET) imaging of LS174T colon adenocarcinoma tumor implants in xenograft mice: preliminary results, World J. Surg. Oncol., 8:65 (2010).

\* cited by examiner

*Primary Examiner* — D L Jones
(74) *Attorney, Agent, or Firm* — Meunier Carlin & Curfman LLC

(57) ABSTRACT

Compositions and methods for evaluating a pharmacokinetic property of an ophthalmic agent administered by intravitreal injection are provided.

2 Claims, 6 Drawing Sheets

PHARMACOKINETIC DETERMINATION OF INTRAVITREAL AGENTS

CROSS-REFERENCE TO RELATED APPLICATIONS

This application claims benefit of U.S. Provisional Application No. 61/637,318, filed Apr. 24, 2012, which is hereby incorporated herein by reference in its entirety.

BACKGROUND

The use of intravitreally placed pharmaceutical agents that inhibit vascular endothelial growth factor (VEGF) is currently the most common form of treatment for neovascular age-related macular degeneration (AMD) and for macular edema secondary to central and branch retinal vein occlusion. Bevacizumab (Avastin®, Genentech) is widely used on an off-label basis in the treatment of neovascular AMD. In addition, ranibizumab (Lucentis®, Genentech) has recently been approved by the US Food and Drug Administration for the treatment of macular edema secondary to central and branch retinal vein occlusion. Both ranibizumab and bevacizumab are widely used off-label for the treatment of diabetic macular edema in the United States. In clinical practice they are injected intravitreally at a frequency no sooner than every 4 weeks for ranibizumab and every 4 to 6 weeks for bevacizumab. Aflibercept (Eylea®, Regeneron) is the newest FDA-approved anti-VEGF agent used for the treatment of exudative AMD. In clinical regimens, aflibercept is typically used for treatment every 4 to 8 weeks.

Intravitreal injection of anti-VEGF agents is the most commonly performed procedure in the treatment of the retina. Systemic side effects have been described with the use of both agents. Ranibizumab has been associated with an increased risk for nonocular hemorrhages (ecchymoses, gastrointestinal hemorrhages, hematoma, vaginal hemorrhages, subdural hematomas), most notably stroke (Rosenfeld P J, et al. *N Engl J Med.* 2006 355:1419-1431; Brown D M, et al. *N Engl J Med.* 2006 355:1432-1444). It may be that the treated population is at increased risk for stroke and that patients with a history of stroke appear to be more susceptible (Boyer D S, et al. *Ophthalmology.* 2009 116: 1731-1739; Ueta T, et al. *Ophthalmology.* 2010 117:1860; Tolentino M. *Surv Ophthalmol.* 2011 56:95-113). Although the systemic use of bevacizumab has been associated with multiple systemic side effects, including hypertension, proteinuria, wound healing complications, GI perforation, nonocular hemorrhages, and thromboembolic events, these effects have not been systematically studied with intravitreal use and await validation in upcoming clinical trials (Yang J C, et al. *N Engl J Med.* 2003 359:427-434; Shah M A, et al. *J Clin Oncol.* 2005 23:2574-2576; Lordick F, et al. *Int J Radiat Oncol Biol Phys.* 2006 64:1295-1298; Gordon C R, et al. *Ann Plast Surg.* 2009 62:707-709).

A clinical question that often arises is whether anti-VEGF agents actually remain within the vitreous cavity after intravitreal placement. It remains uncertain whether significant escape occurs from the vitreous cavity into the systemic circulation or into the central nervous system through the optic nerve that may account for systemic side effects. Furthermore, it is unclear whether these agents actually remain in the vitreous cavity for the duration of the 4- to 6-week treatment interval. In addition, the clinical question often arises whether or not the clearance rate of intravitreally placed anti-VEGF agents is more rapid if the treated eye has undergone previous lens or vitreous removal.

Previous pharmacokinetic studies on animal models to determine the intravitreal duration and half-lives of these agents have relied primarily on serial immunoassay measurements from different animals at different time intervals after intravitreal injection rather than serial measurements over time from the same animals (Bakri S J, et al. *Ophthalmology.* 2007 114:855-859; Bakri S J, et al. *Ophthalmology.* 2007 114:2179-2182; Kim H, et al. *Exp Eye Res.* 2006 82:760-762; Gaudreault J, et al. *Invest Ophthalmol Vis Sci.* 2005 46:726-733). Improved methods for performing pharmacokinetic studies on intravitreally administered agents are needed.

SUMMARY

Methods for evaluating a pharmacokinetic property of an ophthalmic agent are provided. The methods can involve administering a composition containing the ophthalmic agent radiolabeled with a positron-emitting radionuclide into the vitreous cavity of the eye of a subject, serially imaging the eye of the subject to detect positron emission levels in the vitreous cavity of the eye over a period of time, and calculating a pharmacokinetic property of the ophthalmic agent from the measured positron emission levels.

Also provided are methods that involve administering a composition containing a positron-emitting radionuclide with a half-life between about 1 to about 10 days into the vitreous cavity of the eye of a subject, and imaging the eye of the subject to detect positron emission levels in the vitreous cavity of the eye.

Further provided are methods for detecting the location of an ophthalmic agent in the eye that involve administering a composition containing the ophthalmic agent radiolabeled with a positron-emitting radionuclide into the vitreous cavity of the eye of a subject, and imaging the eye of the subject to detect positron emission levels in the vitreous cavity of the eye.

In some embodiments, the ophthalmic agent is an antibody, a recombinant fusion protein, or a small molecule. For example, the ophthalmic agent can be an antibody that specifically binds vascular endothelial growth factor (VEGF), platelet-derived growth factor (PDGF). Non-limiting examples of antibodies that bind VEGF include bevacizumab and ranibizumab. In some cases, the antibody is a bivalent antibody that specifically binds VEGF and PDGF. Suitable antibodies include intact immunoglobulin as well as Fab, Fv, scFv, diabody, triabody, and tetrabody fragments. In some embodiments, the ophthalmic agent can be a recombinant fusion protein that binds VEGF, PDGF, or a combination thereof. In some embodiments, the ophthalmic agent is aflibercept.

In each of the above methods, the positron emission levels can be detected by positron emission tomography-computed tomography (PET-CT). Since the intravitreal half-lives of agents tested have been found to range between 1.5 and 5.0 days, and the studied subjects are ideally quarantined for a period of 10 half-lives before release, the positron-emitting radionuclide preferably have a half-life in the range of about 2.0 to about 10 days, including between about 3 to about 5 days, such as about 4 days. For example, the positron-emitting radionuclide can be iodine-124 ($^{124}$I), manganese-52 ($^{52}$Mn) or Thulium-167 ($^{167}$Tm) which have half-lives of 4.18, 5.59 and 9.25 days, respectively.

Non-limiting examples of pharmacokinetic properties that can be calculated by the disclosed method include clearance, elimination half-life, intravitreal half-life, elimination rate constant, area under the intravitreal concentration curve, or a combination thereof.

The subject of the disclosed method can be any mammal, such as a rodent or primate. However, in particular embodiments, the subject has been diagnosed with a retinal disease. For example, the retinal disease can be a form of macular degeneration (e.g., age-related macular degeneration (AMD), wet macular degeneration, or dry macular degeneration), diabetic retinopathy, retinal vein occlusion, presumed ocular histoplasmosis syndrome, myopic degeneration, endophthalmitis, or uveitis.

In some embodiments, the eye of the subject has undergone an ocular surgery. For example, the eye of the subject may have undergone a vitrectomy, lensectomy, or a combination thereof. Therefore, in some cases, the eyes of subjects may be aphakic, pseudophakic and/or vitrectomized.

Also disclosed is a dosage unit containing an ophthalmic agent radiolabeled with a positron-emitting radionuclide in an amount effective to treat a retinal disease.

The details of one or more embodiments of the invention are set forth in the accompanying drawings and the description below. Other features, objects, and advantages of the invention will be apparent from the description and drawings, and from the claims.

DETAILED DESCRIPTION

Compositions

Figure 1:
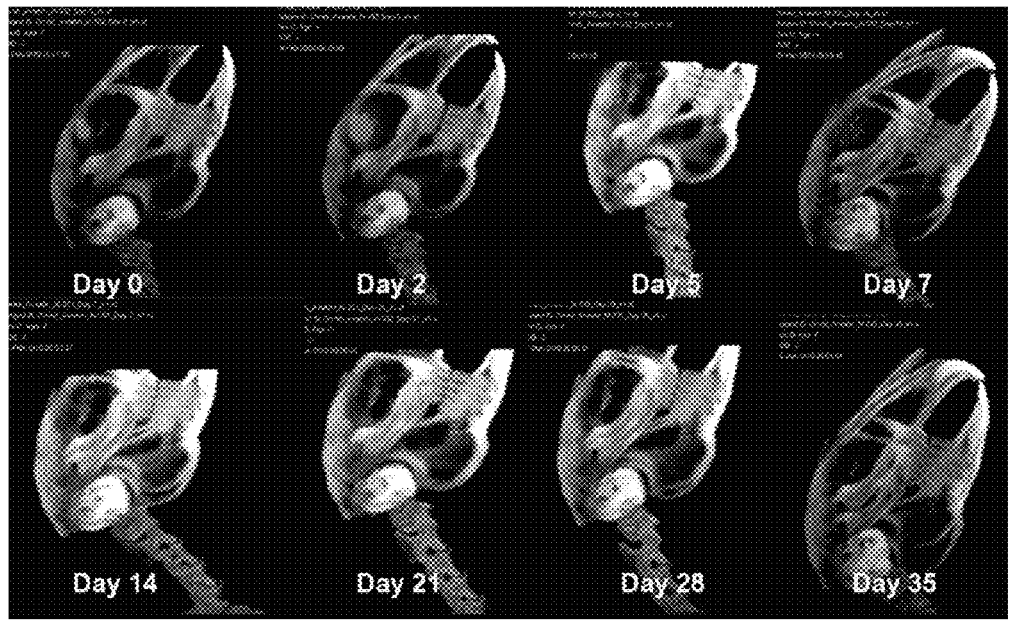
FIG. 1 is an image montage illustrating clearance patterns of I-124 bevacizumab within the vitreous cavity in a rabbit model. The agent is still discernible on day 21 but not detectable on day 28. Range of acquisition of radioactive emission was 10% to 75%.

Disclosed are compositions containing an ophthalmic agent radiolabeled with a positron-emitting radionuclide. Also disclosed are dosage units of the radiolabeled ophthalmic agent in therapeutically effective amount to treat a retinal disease.

In some embodiments, the ophthalmic therapeutic agent of the disclosed compositions and methods relate to any therapetuic agent that can be administered by intravitreal injection. Intravitreal drug therapy was first used over 30 years ago, when antibiotics were injected into the eye to treat vision threatening eye infections. These injections were shown to be safe and effective.

There are a number of medications now available for treatment of retinal disease. These medications work by reducing macular edema, stopping abnormal blood vessel growth, or reducing intraocular inflammation. Therefore, non-limiting examples of ophthalmic agents include anti-angiogenesis agents, anti-glaucoma agents, anti-infective agents, anti-inflammatory agents, growth factors, immunosuppressant agents, anti-allergic agents, and combinations thereof.

Representative anti-angiogenesis agents include, but are not limited to, antibodies to vascular endothelial growth factor (VEGF) such as bevacizumab (Avastin®, Genentech) and ranibizumab (Lucentis®, Genentech), and other anti-VEGF compounds including aflibercept (Eylea®, Regeneron); pegaptanim sodium (anti-VEGF aptamer, Macugen®, Eyetech Pharmaceuticals); pigment epithelium derived factor(s) (PEDF); COX-2 inhibitors such as celecoxib (Celebrex®, G. D. Searle & Co.) and rofecoxib (Vioxx™, Merck & Co., Inc); interferon alpha; interleukin-12 (IL-12); thalidomide (Thalomid®, Celgene Corporation) and derivatives thereof such as lenalidomide (Revlimid®, Celgene Corporation); squalamine; endostatin; angiostatin; ribozyme inhibitors such as Angiozyme™ (Sirna Therapeutics); multifunctional antiangiogenic agents such as AE-941 (Neovastat™, Aeterna Laboratories); receptor tyrosine kinase (RTK) inhibitors such as sunitinib (Sutent®, Pfizer); tyrosine kinase inhibitors such as sorafenib (Nexavar®, Bayer) and erlotinib (Tarceva®, OSI Phamaceuticals); antibodies to the epidermal grown factor receptor such as panitumumab (Vectibix®, Immunex Corp.) and cetuximab (Erbitux®, ImClone Systems Inc.), as well as other anti-angiogenesis agents known in the art.

Representative anti-glaucoma agents include prostaglandin analogs (such as travoprost, bimatoprost, and latanoprost), beta-andrenergic receptor antagonists (such as timolol, betaxolol, levobetaxolol, and carteolol), alpha-2 adrenergic receptor agonists (such as brimonidine and apraclonidine), carbonic anhydrase inhibitors (such as brinzolamide, acetazolamine, and dorzolamide), miotics (i.e., parasympathomimetics, such as pilocarpine and ecothiopate), seretonergics muscarinics, dopaminergic agonists, and adrenergic agonists (such as apraclonidine and brimonidine).

Anti-infective agents include antiviral agents, antibacterial agents, antiparasitic agents, and anti-fungal agents. Representative antiviral agents include ganciclovir and acyclovir. Representative antibiotic agents include aminoglycosides such as streptomycin, amikacin, gentamicin, and tobramycin, ansamycins such as geldanamycin and herbimycin, carbacephems, carbapenems, cephalosporins (e.g., cefazolin and cefatazidime), glycopeptides such as vancomycin, teicoplanin, and telavancin, lincosamides, lipopeptides such as daptomycin, macrolides such as azithromycin, clarithromycin, dirithromycin, and erythromycin, monobactams, nitrofurans, penicillins, polypeptides such as bacitracin, colistin and polymyxin B, quinolones, fluoroquinolones (e.g., ciprofloxacin), sulfonamides, and tetracyclines. Representative anti-fungal agent include polyene antifungal drugs such as amphotericin-B.

In some cases, the active agent is an anti-allergic agent such as olopatadine and epinastine.

Anti-inflammatory agents include both non-steroidal and steroidal anti-inflammatory agents. Suitable steroidal active agents include glucocorticoids, progestins, mineralocorticoids, and corticosteroids. For example, the ophthalmic agent can be triamcinolone acetonide, which is a synthetic corticosteroid that is administered by intravitreal injection to treat macular edema.

In particular embodiments, the ophthalmic agent is an antibody. For example, the ophthalmic agent can be an antibody that specifically binds vascular endothelial growth factor (VEGF), platelet-derived growth factor (PDGF). In some cases, the antibody is a bivalent antibody that specifically binds VEGF and PDGF. Non-limiting examples of antibodies that bind VEGF include bevacizumab and ranibizumab.

In some embodiments, the ophthalmic agent is a fusion protein that binds Sphingosine-1-phosphate (S1P), which has also been shown to be involved in ocular disease, such as AMD, choroidal neovascularization, and cancer. Anti-S1P antibodies are described in US 2013/0058951, which is incorporated by reference for the teaching of these antibodies.

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. The variability is typically concentrated in three segments called complementarity determining regions (CDRs) or hypervariable regions both in the light chain and the heavy chain variable domains. Therefore, in some embodiments, the disclosed antibodies contain at least the CDRs necessary to maintain DNA binding and/or interfere with DNA repair.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the non-modified antibody or antibody fragment.

Techniques can also be adapted for the production of single-chain antibodies specific to an antigenic protein of the present disclosure. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

In some embodiments, the antibody is a monoclonal antibody. The antibody can also be a "chimeric" antibody in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The antibodies may also be made by recombinant DNA methods. DNA encoding the disclosed antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment.

The disclosed antibody may be a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

The ophthalmic agent can also be a recombinant fusion protein. Fusion proteins, also known as chimeric proteins, are proteins created through the joining of two or more genes which originally coded for separate proteins. Translation of this fusion gene results in a single polypeptide with function properties derived from each of the original proteins. Recombinant fusion proteins can be created artificially by recombinant DNA technology for use in biological research or therapeutics.

The functionality of fusion proteins is made possible by the fact that many protein functional domains are modular. In other words, the linear portion of a polypeptide which corresponds to a given domain, such as a tyrosine kinase domain, may be removed from the rest of the protein without destroying its intrinsic enzymatic capability. Thus, any of the herein disclosed functional domains can be used to design a fusion protein.

A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either. Often linker (or spacer) peptides are also added which make it more likely that the proteins fold independently and behave as expected.

In some embodiments, the ophthalmic agent is a fusion protein that binds VEGF, PDGF, or a combination thereof. For example, the fusion protein can contain a receptor, or receptor domain, that binds VEGF, PDGF, or a combination thereof. For example, the ophthalmic agent be a fusion protein of domain 2 from VEGFR1 and domain 3 from VEGFR2. This recombinant fusion protein has a high affinity for VEGF and interacts with all VEGF isoforms as well as placental growth factors. As an example, the ophthalmic agent can be aflibercept (VEGF trap-eye).

The ophthalmic agent can be a functional nucleic acid. Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, RNAi, and external guide sequences. The functional nucleic acid molecules can act as affectors, inhibitors, modulators, and stimulators of a specific activity possessed by a target molecule.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $K_d$'s from the target molecule of less than 10-12 M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. For example, pegaptanim sodium (anti-VEGF aptamer, Macugen®, Eyetech Pharmaceuticals) is a pegylated anti-VEGF aptamer that can be used as an anti-angiogenic medicine for the treatment of neovascular (wet) age-related macular degeneration (AMD).

Gene expression can also be effectively silenced in a highly specific manner through RNA interference (RNAi). This silencing was originally observed with the addition of double stranded RNA (dsRNA). Once dsRNA enters a cell, it is cleaved by an RNase III—like enzyme, Dicer, into double stranded small interfering RNAs (siRNA) 21-23 nucleotides in length that contains 2 nucleotide overhangs on the 3' ends. In an ATP dependent step, the siRNAs become integrated into a multi-subunit protein complex, commonly known as the RNAi induced silencing complex (RISC), which guides the siRNAs to the target RNA. At some point the siRNA duplex unwinds, and it appears that the antisense strand remains bound to RISC and directs degradation of the complementary mRNA sequence by a combination of endo and exonucleases. However, the effect of iRNA or siRNA or their use is not limited to any type of mechanism. In one example, an siRNA triggers the specific degradation of homologous RNA molecules, such as mRNAs, within the region of sequence identity between both the siRNA and the target RNA. Sequence specific gene silencing can be achieved in mammalian cells using synthetic, short double-stranded RNAs that mimic the siRNAs produced by the enzyme dicer. siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit. The production of siRNA from a vector is more commonly done through the transcription of a short hairpin RNAs (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. Disclosed herein are any shRNA designed as described above based on the sequences for the herein disclosed inflammatory mediators.

In some embodiments, the ophthalmic agent is an siRNA that inhibits HIF-1 alpha ore ICAM-1 gene expression. US 2012/0308645 describes siRNAs that inhibit HIF-1 alpha gene expression to inhibit angiogenesis, in particularly in diseases such as diabetic retinopathy, age related macular degeneration and many types of cancer. US 2012/0276192 describes siRNAs that inhibit ICAM-1 gene expression to treat diseases that involve ICAM-1-mediated cell adhesion, such as diabetic retinopathy and age related macular degeneration. Each of these patent publications are incorporate by reference for the teaching of siRNA ophthalmic agents.

In some embodiments, the ophthalmic agent is a small molecule. Suitable small molecule active agents include organic and organometallic compounds. In some instances, the small molecule active agent has a molecular weight of less than about 2000 g/mol, more preferably less than about 1500 g/mol, most preferably less than about 1200 g/mol. The small molecule active agent can be a hydrophilic, hydrophobic, or amphiphilic compound.

In some cases, the ophthalmic agent is a small molecule that inhibits the tyrosine kinase receptors stimulated by VEGF. For example, sunitinib (Sutent®, SU11248, Pfizer), a small molecule inhibitor of receptor tyrosine kinases of VEGFR and platelet-derived growth factor receptor, has been approved for the treatment of cancer. The antiangiogenic compound SU5416 (3-[(2,4-dimethylpyrrhol-5-yl) methylidenyl]-indolin-2-one) is a potent and selective inhibitor of VEGFR2. It has been shown to suppress VEGF-mediated angiogenesis through the inhibition of autophosphorylation of VEGFR2 by blocking the adenosine monophosphate-binding site within the kinase domain. PF-00337210 is a VEGF receptor 2 tyrosine kinase inhibitor that was originally developed as an oncology drug and was later considered for the treatment of retinal diseases. Additional small molecules that inhibit tyrosine kinase receptors stimulated by VEGF include apatinib (Tykerb®), sorafenib (Nexavar®), axitinib, and pazopanib.

The elimination of small molecules in solution from the vitreal space is quite rapid, generally with an elimination half-life of less than 60 h from the vitreous. However, liposomal vehicles can be used to prolong clearance of ophthalmic agents after intravitreal injection. Methods of liposomal encapsulation of compounds for intravitreal injection are known in the art.

The disclosed ophthalmic agents may be conjugated to a positron-emitting radionuclide for use in the disclosed compositions and methods.

Positron emission (β+ decay) is a particular type of radioactive decay, and a subtype of beta decay, in which a proton inside a radionuclide nucleus is converted into a neutron while releasing a positron and an electron neutrino. Because positron emission decreases proton number relative to neutron number, positron decay happens typically in large "proton-rich" radionuclides. Positron decay results in nuclear transmutation, changing an atom of a chemical element into an atom of an element with an atomic number that is less by one unit.

The positron-emitting radionuclide preferably has a half-life between about 0.5 to about 10 days, including between about 3 to about 5 days, such as about 4 days. For example, the positron-emitting radionuclide can be iodine-124 ($^{124}$I) or manganese-52 ($^{52}$Mn) or Thulium-167 ($^{167}$Tm).

Positron-emitting radionuclides are typically produced in cyclotrons by the bombardment of stable elements with protons, deuterons, or helium nuclei. The radionuclides produced have an excess of protons and thus decay by the emission of positrons. Due to the short half-lives of the positron-emitting radionuclides, the cyclotron can be located on-site with the PET-CT scanner used in the disclosed methods.

Disclosed are pharmaceutical compositions containing therapeutically effective amounts of one or more of the disclosed radiolabeled ophthalmic agents and a pharmaceutically acceptable carrier. Pharmaceutical carriers suitable for administration of the compounds provided herein include any such carriers known to those skilled in the art to be suitable for the particular mode of administration, such as intravitreal injection. Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials which are generally recognized as safe (GRAS), and may be administered to an individual without causing undesirable biological side effects or unwanted interactions.

In addition, the radiolabeled ophthalmic agents may be formulated as the sole pharmaceutically active ingredient in the composition or may be combined with other active ingredients. For example, the radiolabeled ophthalmic agents may be formulated or combined with known NSAIDs, anti-inflammatory compounds, steroids, and/or antibiotics. In certain embodiments, the pharmaceutical composition contains one or more local anesthetics. Representative local anesthetics include tetracaine, lidocaine, amethocaine, proparacaine, lignocaine, and bupivacaine. In some cases, one or more additional agents, such as a hyaluronidase enzyme, is also added to the formulation to accelerate and improves dispersal of the local anesthetic.

The ophthalmic drug may be present in its neutral form, or in the form of a pharmaceutically acceptable salt. In some cases, it may be desirable to prepare a formulation containing a salt of an active agent due to one or more of the salt's advantageous physical properties, such as enhanced stability or a desirable solubility or dissolution profile.

Generally, pharmaceutically acceptable salts can be prepared by reaction of the free acid or base forms of an active agent with a stoichiometric amount of the appropriate base or acid in water or in an organic solvent, or in a mixture of the two; generally, non-aqueous media like ether, ethyl acetate, ethanol, isopropanol, or acetonitrile are preferred. Pharmaceutically acceptable salts include salts of an active agent derived from inorganic acids, organic acids, alkali metal salts, and alkaline earth metal salts as well as salts formed by reaction of the drug with a suitable organic ligand (e.g., quaternary ammonium salts). Lists of suitable salts are found, for example, in Remington's Pharmaceutical Sciences, 20th ed., Lippincott Williams & Wilkins, Baltimore, Md., 2000, p. 704. Examples of ophthalmic drugs some-times administered in the form of a pharmaceutically acceptable salt include timolol maleate, brimonidine tartrate, and sodium diclofenac.

Pharmaceutical formulations for ocular administration are preferably in the form of a sterile aqueous solution or suspension. Acceptable solvents include, for example, water, Ringer's solution, phosphate buffered saline (PBS), and isotonic sodium chloride solution. The formulation may also be a sterile solution, suspension, or emulsion in a nontoxic, parenterally acceptable diluent or solvent such as 1,3-butanediol.

In some instances, the formulation is distributed or packaged in a liquid form. Alternatively, formulations for ocular administration can be packed as a solid, obtained, for example by lyophilization of a suitable liquid formulation. The solid can be reconstituted with an appropriate carrier or diluent prior to administration.

Solutions, suspensions, or emulsions for ocular administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for ocular administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for ocular administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

In some embodiments, the ophthalmic agents are formulated for single dosage intravitreal administration. For example, intravitreal doses and volumes of anti-VEGF agents are typically 40-320 times lower than those used systemically. For example, a typical intravitreal dosage of avastin in the clinic is 1.25 mg/0.05 mL as compared to intravenous doses of 100 mg/4 mL or 400 mg/16 mL.

To formulate a composition, the weight fraction of ophthalmic agents is dissolved, suspended, dispersed or otherwise mixed in a selected carrier at a therapeutically effective concentration and amount. The radiolabeled ophthalmic agents are included in the pharmaceutically acceptable carrier in an amount sufficient to exert a therapeutically useful effect in the absence of undesirable side effects on the patient treated. The therapeutically effective concentration may be determined empirically by testing the ophthalmic agents in in vitro, ex vivo and in vivo systems, and then extrapolated therefrom for dosages for humans. The concentration of radiolabeled ophthalmic agents in the pharmaceutical composition will depend on absorption, inactivation and excretion rates of the active compound, the physicochemical characteristics of the compound, the dosage schedule, and amount administered as well as other factors known to those of skill in the art.

Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the ophthalmic agents or a combination of essential ingredients per dosage unit form.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Liquid pharmaceutically administrable compositions can, for example, be prepared by dissolving, dispersing, or otherwise mixing a radiolabeled ophthalmic agents as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of non-toxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, or in one embodiment 0.1-95%.

Injectables can be prepared in conventional forms, either as liquid solutions or suspensions, solid forms suitable for solution or suspension in liquid prior to injection, or as emulsions. The injectables, solutions and emulsions also contain one or more excipients.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include sodium chloride injection, ringers injection, isotonic dextrose injection, sterile water injection, dextrose and lactated ringers injection. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment. The concentration of the pharmaceutically active compound is adjusted so that an injection provides an effective amount to produce the desired pharmacological effect. The exact dose depends on the age, weight and condition of the patient or animal as is known in the art.

A unit-dose parenteral preparation can be packaged in an ampoule, a vial or a syringe with a needle. All preparations for parenteral administration should be sterile, as is known and practiced in the art.

The radiolabeled ophthalmic agents may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle.

Methods

Methods for evaluating a pharmacokinetic property of an ophthalmic agent are provided. The methods can involve administering a composition containing the ophthalmic agent radiolabeled with a positron-emitting radionuclide into the vitreous cavity of the eye of a subject, serially imaging the eye of the subject to detect positron emission levels in the vitreous cavity of the eye over a period of time, and calculating a pharmacokinetic property of the ophthalmic agent from the measured positron emission levels.

Also provided are methods that involve administering a composition containing a positron-emitting radionuclide with a half-life between about 1 to about 10 days into the vitreous cavity of the eye of a subject, and imaging the eye of the subject to detect positron emission levels in the vitreous cavity of the eye.

Further provided are methods for detecting the location of an ophthalmic agent in the eye that involve administering a composition containing the ophthalmic agent radiolabeled with a positron-emitting radionuclide into the vitreous cavity of the eye of a subject, and imaging the eye of the subject to detect positron emission levels in the vitreous cavity of the eye.

In each of the above methods, the positron emission levels can be detected by positron emission tomography (PET). PET is a nuclear medical imaging technique that produces a three-dimensional image of functional processes in the body. The system detects pairs of gamma rays emitted indirectly by a positron-emitting radionuclide. Three-dimensional images of radionuclide concentration within the body are then constructed by computer analysis.

As the radioisotope undergoes positron emission decay ($\beta$+ decay), it emits a positron, an antiparticle of the electron with opposite charge. The emitted positron travels in tissue for a short distance (typically less than 1 mm), during which time it loses kinetic energy, until it decelerates to a point where it can interact with an electron. The encounter annihilates both electron and positron, producing a pair of annihilation ($\gamma$) photons moving in approximately opposite directions. These are detected when they reach a scintillator in the scanning device, creating a burst of light which is detected by photomultiplier tubes or silicon avalanche photodiodes. The technique depends on simultaneous or coincident detection of the pair of photons moving in approximately opposite direction. Photons that do not arrive in temporal "pairs" (i.e. within a timing-window of a few nanoseconds) can be ignored.

PET scans are increasingly read alongside computed tomography (CT) or magnetic resonance imaging (MRI) scans, with the combination (called "co-registration") giving both anatomic and metabolic information. Because PET imaging is most useful in combination with anatomical imaging, such as CT, modern PET scanners are now available with integrated high-end multi-detector-row CT scanners (so-called "PET/CT").

The subject of the disclosed method can be any mammal, such as a rodent or primate. However, in particular embodiments, the subject has been diagnosed with a retinal disease. For example, the retinal disease can be a form of macular degeneration (e.g., age-related macular degeneration (AMD), wet macular degeneration, or dry macular degeneration), diabetic retinopathy, retinal vein occlusion, endophthalmitis, or uveitis. In some embodiments, the eye of the subject has undergone an ocular surgery. For example, the eye of the subject may have undergone a vitrectomy, lensectomy, or a combination thereof. Therefore, in some cases, the subject is aphakic The disclosed methods allow for evaluation of one or more pharmacokinetic properties of an ophthalmic agent. Non-limiting examples of pharmacokinetic properties that can be calculated by the disclosed method include clearance, elimination half-life, intravitreal half-life, elimination rate constant, area under the intravitreal concentration curve, or a combination thereof.

Pharmacokinetic analysis is performed by noncompartmental or compartmental methods. Noncompartmental methods estimate the exposure to a drug by estimating the area under the curve of a concentration-time graph. Compartmental methods estimate the concentration-time graph using kinetic models. Bioanalytical methods are necessary to construct a concentration-time profile.

In some embodiments, the pharmacokinetic property is intravitreal half-life of the opthalmic agent. For example, the intravitreal half-life of each agent can be calculated using the following formula for first-order kinetics:

$$T_{1/2} = (T \times \log 2)/(\log [Drug]_b/[Drug]_e)$$

where $T_{1/2}$ is the half-life, T is the elapsed time, $[Drug]_b$=Beginning Amount, and $[Drug]_e$=Ending Amount.

The disclosed compositions and methods involve intravitreal injection of a therapeutically effective amount of one or more ophthalmic agents radiolabeled with a positron-emitting radionuclide as disclosed herein.

For intravitreal injection, there is general agreement that the injection site should be located 3.5 to 4 mm posterior to the limbus. The injection site preferably differs in repeated injections to avoids a double penetration through the same site, inducing a persisting scleral hole with consecutive leaking or vitreous incarceration "vitreous wick." The angle of the incision through the sclera may be directed in an oblique, tunneled fashion, as rectangular radial incisions may remain open, inducing vitreous or drug reflux under the conjunctiva, as well as severe chemosis and even hypotony in vitrectomized eyes. The depth of the insertion may vary between 5 to 7 mm, so that the tip of the needle is placed in the mid-vitreous. The ophthalmic agent may then be gently injected into the vitreous cavity.

The needle diameter should be smaller than 27-gauge to reduce risk of wound leakage or injury. The required force to penetrate the sclera is almost twice as much using 27-gauge needles compared with 30- or even 31-gauge. Larger needles may not necessarily induce more pain to the patient; however, they may induce more reflux or subconjunctival hemorrhage. In addition, blunting of the needle tip, as found in some prefilled syringes, has been observed to cause a deeper inpouching and visible indentation of the eye wall during the injection that may have caused the patient more discomfort. The injected volume should be limited up to 0.15 ml without a routine paracentesis releasing an elevated ocular pressure. Administration of rTPA, anti-VEGF agents, and SF6 gas as triple injection for the management of subretinal hemorrhage frequently require a paracentesis to release the elevated eye pressure.

Satisfactory pain relief may be achieved with topical lidocaine. Local anesthesia may be induced by applying 3 to 4 sterile cotton swabs soaked in sterile 4% lidocaine to the injection area (for 30 seconds each). Alternatively, lidocaine may be applied with 2% eyedrops, as a gel, or as a subconjunctival injection. The effective relief of pain with lidocaine for intravitreal injection seems to be independent of its mode of application. However, topical applications of lidocaine cause less chemosis compared with subconjunctival anaesthesia. Topical antibiotics can be used preoperatively and/or postoperatively.

Definitons

The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

A "chimeric molecule" is a single molecule created by joining two or more molecules that exist separately in their native state. The single, chimeric molecule has the desired functionality of all of its constituent molecules.

A "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The terms "peptide," "protein," and "polypeptide" are used interchangeably to refer to a natural or synthetic molecule comprising two or more amino acids linked by the carboxyl group of one amino acid to the alpha amino group of another. In addition, as used herein, the term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini.

The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ϵ-amino caproic acid, 7-amino heptanoic acid, L-aspartic acid, L-glutamic acid, N-ϵ-Boc-N-α-CBZ-L-lysine, N-ϵ-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "protein domain" refers to a portion of a protein, portions of a protein, or an entire protein showing structural integrity; this determination may be based on amino acid composition of a portion of a protein, portions of a protein, or the entire protein.

The term "small molecule" refers to a molecule, such as an organic or organometallic compound, with a molecular weight of less than 2,000 Daltons, more preferably less than 1,500 Daltons, most preferably less than 1,000 Daltons. The small molecule can be a hydrophilic, hydrophobic, or amphiphilic compound.

The term "specifically binds", as used herein, when referring to a polypeptide (including antibodies) or receptor (including fragments and fusion proteins), refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ M$^{-1}$ (e.g., $10^6$ M$^{-1}$, $10^7$ M$^{-1}$, $10^8$ M$^{-1}$, $10^9$ M$^{-1}$, $10^{10}$ M$^{-1}$, $10^{11}$ M$^{-1}$, and $10^{12}$ M$^{-1}$ or more) with that second molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "variant" refers to an amino acid or peptide sequence having conservative amino acid substitutions, non-conservative amino acid substitutions (i.e. a degenerate variant), substitutions within the wobble position of each codon (i.e. DNA and RNA) encoding an amino acid, amino acids added to the C-terminus of a peptide, or a peptide having 60%, 70%, 80%, 90%, or 95% homology to a reference sequence.

EXAMPLES

Example 1

PET/CT Imaging of I-124-Radiolabeled Bevacizumab and Ranibizumab after Intravitreal Injection in a Rabbit Model The use of positron emission tomography (PET)/computed tomography (CT) offers a unique approach to directly and noninvasively visualize radiolabeled anti-VEGF agents in the vitreous cavity and to determine their pharmacokinetic properties. PET is a nuclear medicine imaging technique that produces a three-dimensional image of a functional process within the body. It detects pairs of gamma rays that are emitted by a positron-emitting radionuclide. Biologically active molecules can then be detected by labeling with a positron-emitting radionuclide such as I-124. Images of radionuclide concentrations can then be reconstructed three-dimensionally by computer analysis. The coregistration of PET and CT scans allows for the two scans to be performed in immediate sequence, enabling precise correlation of functional and anatomic imaging during the same scan session.

PET/CT was used to image intravitreally placed I-124-radiolabeled bevacizumab and ranibizumab in a rabbit model. Whether intravitreally placed anti-VEGF agents remain within the vitreous cavity after injection was determined. The pharmacokinetic properties of these two agents were studied by sequential ocular imaging of the animals over time. The serial methods were validated by studying agents with well-known half-lives.

Materials and Methods

Radiolabeling of bevacizumab and ranibizumab with I-124 (IBA Molecular, Dulles, Va.) was completed using a modified Iodogen method, described previously (Zou P, et al. World J Surg Oncol. 2010 8:65). Radiochemical purity for I-124-labeled bevacizumab and I-124-labeled ranibizumab was found to be 95% and 98%, respectively.

All treatments were conducted in agreement with the ARVO Statement for the Use of Animals in Ophthalmic and Vision Research. All experimental protocols were approved, and the procedures followed were in accordance with the ethical standards of the Institutional Animal Care and Use Committee at The Ohio State University. Six male Dutch-belted rabbits (Myrtle's Rabbitry, Thompsons Station, Tenn.) weighing 1.5 to 1.8 kg each were used for this study. The rabbits were anesthetized with intramuscularly placed xylazine (0.1-0.2 mL; 5 mg/mL) and ketamine hydrochloride (1.7 mL; 100 mg/mL). Intravitreal injection consisting of 0.5 mg/0.05 mL I-124-labeled ranibizumab or 1.25 mg/0.05 mL I-124-labeled bevacizumab was placed 1 mm posterior to the limbus of the left eye in three rabbits for each of the two agents.

The anesthetized rabbits were then lightly secured to the scanner bed with elastic socks or gauze for the purpose of imaging. The animals were imaged for 10 minutes in the micro-PET/CT (Inveon; Siemens Preclinical, Knoxyille, Tenn.), followed by an attenuation scan for 15 minutes. Micro-PET scans each resulted in a reconstructed volume with an effective pixel size of 0.78 mm. Micro-CT had an effective pixel size of 0.099 mm. The scans were performed on days 0, 2, 5, 7 and then weekly. Imaging was discontinued 1 week after the radiolabeled agent was undetectable, which occurred on day 28 for ranibizumab and on day 35 for bevacizumab. After the last imaging session, the anesthetized rabbits were euthanatized by intravenous injection of 3 mL saturated KCl.

The radioactive units, in becquerels per milliliter, obtained at each time point were modified with a correction factor to account for radioactive decay of I-124. Resultant measurements were used to formulate the retention curves and to calculate the intravitreal half-lives of each agent. The half-life of each agent was calculated using the following formula for first-order kinetics:

$T_{1/2} = (T \times \log 2)/(\log [Drug]_b/[Drug]_e)$ where $T_{1/2}$ is the half-life, T is the elapsed time, $[Drug]_b$=Beginning Amount, and $[Drug]_e$=Ending Amount.

Results

Escape from the Vitreous Cavity

Figure 2:
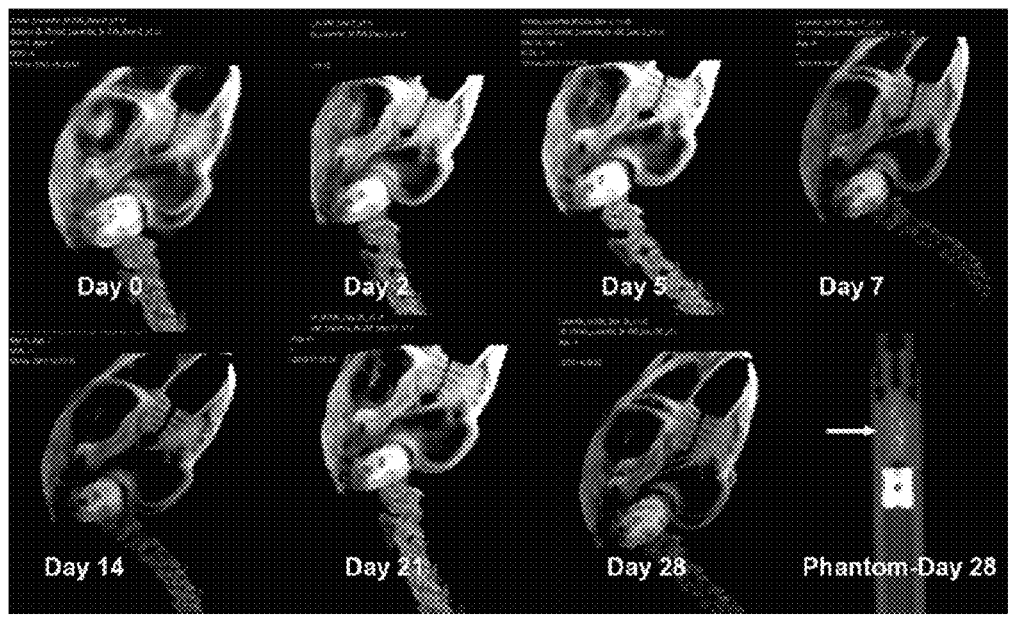
FIG. 2 is an image montage illustrating clearance pattern of I-124 ranibizumab within the vitreous cavity over time in a rabbit model. The agent is still discernible on day 14 but not detectable on day 21. A phantom containing I-124 ranibizumab in a tuberculin syringe is easily discerned on day 28 (arrow), indicating that the lack of positron emission in the vitreous cavity was due to ranibizumab clearance rather than to I-124 decay. Range of acquisition of radioactive emission was 10% to 75%.

In all six rabbits, I-124 bevacizumab and I-124 ranibizumab were not detectable outside the vitreous cavity and the thyroid for the length of the study after intravitreal injection. None of the eyes developed evidence of endophthalmitis, uveitis, cataract, or other adverse events during the study. The two montages illustrate serial images for each agent over time (FIGS. 1, 2). Radioactive emission was set at a range of 10% to 75% for all the figures to eliminate noise and to provide for a consistent range of emission for all the figures. Although there was discernible anatomic localization within the eye at lower emission thresholds, background noise levels were increased.

Figure 3:
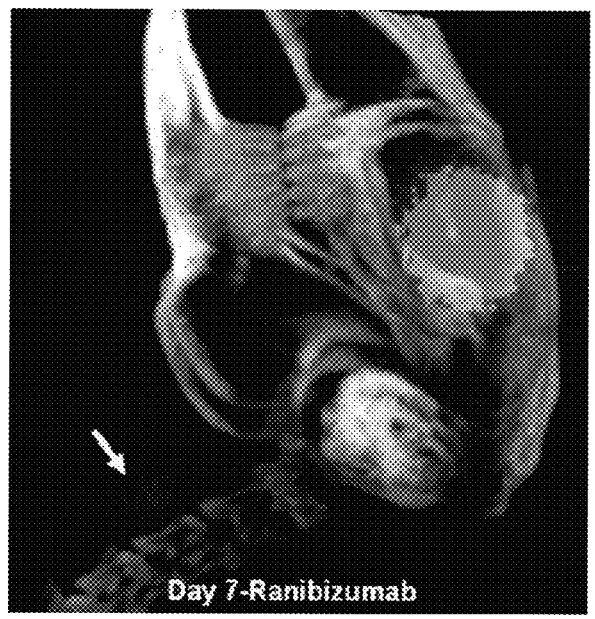
FIG. 3 shows I-124 accumulation in the thyroid gland at day 7 (arrow). Range of acquisition of radioactive emission was set between 2% and 25% to allow for lower levels of detection.

Ranibizumab and bevacizumab were visible until days 14 and 21 and detectable until day 21 and 28, respectively. Any further detection beyond these days was compatible with background noise. Intravitreal levels of radioactivity, in becquerels per milliliter, are listed for each rabbit in Table 1. Accumulation of I-124 in the thyroid gland was visible at lower emission thresholds (FIG. 3). For both agents, I-124 was not visible in the thyroid on day 0, peaked on day 2 and was last detectable on day 14 for five rabbits (Table 2). The sixth rabbit had the highest intravitreal I-124 levels on day 0, and I-124 remained detectable in the thyroid until day 21.

TABLE 1

Intravitreal Radioactivity Levels (Bq/mL)

| Day | Bev 1 | Bev 2 | Bev 3 | Ran 1 | Ran 2 | Ran 3 |
|---|---|---|---|---|---|---|
| 0 | 175370.0 | 205250.0 | 178970.0 | 167730.0 | 116000.0 | 164540.0 |
| 2 | 84861.5 | 106740.0 | 89862.3 | 89780.3 | 50111.7 | 69510.8 |
| 5 | 31247.2 | 38312.8 | 33722.5 | 21029.2 | 14030.5 | 19604.7 |
| 7 | 15523.8 | 19824.4 | 17006.6 | 5933.5 | 5946.1 | 8350.8 |
| 14 | 1549.1 | 1929.9 | 1695.3 | 470.6 | 275.7 | 454.5 |
| 21 | 174.5 | 44.3 | 161.4 | 31.6 | 16.7 | 31.1 |
| 28 | 17.2 | 23.8 | 15.9 | 4.9 | 8.2 | 9.1 |
| 35 | 7.6 | 5.1 | 9.1 | | | |

Bev, bevacizumab;
Ran, ranibizumab.

TABLE 2

Thyroid Radioactivity Levels (Bq/mL)

| Day | Bev 1 | Bev 2 | Bev 3 | Ran 1 | Ran 2 | Ran 3 |
|---|---|---|---|---|---|---|
| 2 | 429.4 | 490.6 | 351.3 | 475.0 | 410.0 | 464.9 |
| 5 | 311.4 | 388.5 | 272.8 | 321.0 | 416.0 | 367.6 |
| 7 | 224.0 | 323.4 | 217.3 | 207.1 | 297.1 | 294.4 |
| 14 | 77.2 | 113.8 | 71.1 | 43.5 | 71.8 | 59.1 |
| 21 | | 33.6 | | | | |

Bev, bevacizumab;
Ran, ranibizumab.

Pharmacokinetic Properties

Figure 4:
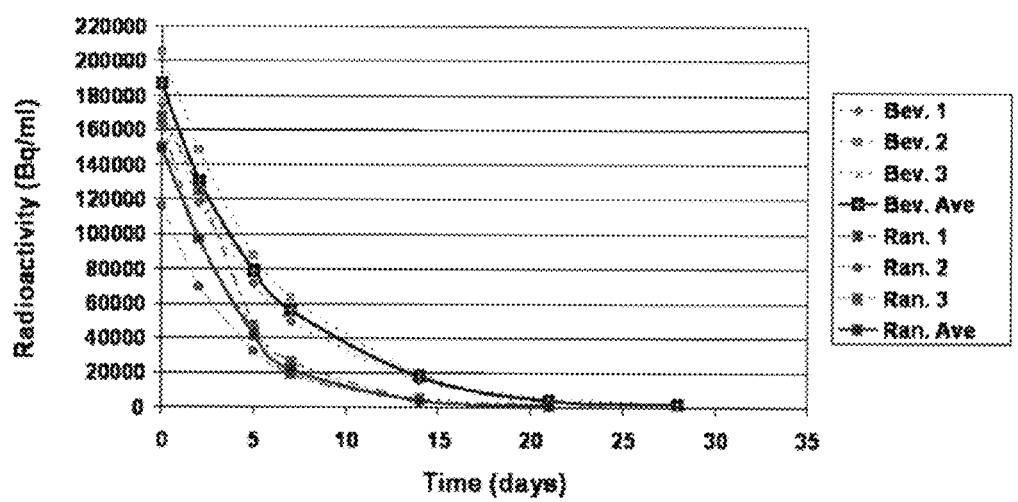
FIG. 4 is a graph demonstrating clearance curves for I-124-labeled bevacizumab and ranibizumab. The units are corrected for I-124 radioactive decay. Curves with dashes represent radioactive emissions of each individual subject. The solid curve represents the average radioactive emission. The curves are consistent with each of the two groups, and bevacizumab is cleared more slowly than ranibizumab. I-124 bevacizumab remains detectable until day 28, whereas I-124 ranibizumab is detectable until day 21.

Resultant clearance patterns were consistent within each of the two agent groups (FIG. 4). I-124 ranibizumab could be imaged on day 28 as a phantom in a syringe though it was not detectable in the vitreous cavity at this time (FIG. 2). For each agent the absorption appeared to fit a two-compartment model with an initial rapid distribution phase until day 5, followed by a slower elimination phase. The average intravitreal half-lives for bevacizumab and ranibizumab after adjustment for radioactive I-124 decay were calculated to be 4.02 (±0.137) and 2.71 (±0.056) days, respectively, for the initial distribution phase and 4.27 (±0.157) and 2.82 (±0.089) days, respectively, for the elimination phase. The overall average intravitreal half-lives of bevacizumab and ranibizumab were 4.22 (±0.124) and 2.81 (±0.083) days, respectively. These values were in agreement with previous works by others (Bakri S J, et al. Ophthalmology. 2007 114:855-859; Bakri S J, et al. Ophthalmology. 2007 114:2179-2182; Kim H, et al. Exp Eye Res. 2006 82:760-762; Gaudreault J, et al. Invest Ophthalmol Vis Sci. 2005 46:726-733).

Discussion

Integrated PET/CT imaging was used to visualize I-124-labeled ranibizumab and bevacizumab in the vitreous cavity after intravitreal injection. There was no evidence of escape of bevacizumab and ranibizumab from the vitreous cavity, though iodine was found to be sequestered in the thyroid gland. The measured intravitreal radioactive emission from these agents allowed for determination of the pharmacokinetic properties of these proteins while in the vitreous cavity. The improvement of integrating PET/CT imaging compared with previous immunoassay methods for the determination of pharmacokinetic properties of intravitreally placed agents lies in its ability to directly and noninvasively visualize the labeled agent and to serially follow the same subject over time.

Concerns have been raised that intravitreal ranibizumab and systemic bevacizumab may predispose patients to stroke and nonocular hemorrhages (Rosenfeld P J, et al. N Engl J Med. 2006 355:1419-1431; Brown D M, et al. N Engl J Med. 2006 355:1432-1444; Yang J C, et al. N Engl J Med. 2003 359:427-434; Shah M A, et al. J Clin Oncol. 2005 23:2574-2576; Lordick F, et al. Int J Radiat Oncol Biol Phys. 2006 64:1295-1298; Gordon C R, et al. Ann Plast Surg. 2009 62:707-709). No evidence of escape of these agents into the central nervous system or elsewhere was found in any of the subjects during the length of the study that could account for these side effects. Once the anti-VEGF agent is absorbed into the bloodstream, I-124 decouples from its substrate and is sequestered in the thyroid gland. These levels were found to be low and not detectable after day 14 in 5 of 6 rabbits. Hematogenous spread is below PET/CT resolution thresholds and cannot be excluded based on these findings. Levels of ranibizumab and bevacizumab were not measured in the bloodstream.

The agents remained detectable only in the vitreous cavity until day 28 (bevacizumab) and day 21 (ranibizumab). The phantom containing ranibizumab was easily detectable at day 28, indicating that the lack of positron emission from the vitreous cavity at this time was likely due to the absorption of ranibizumab rather than to the radioactive decay of I-124. The duration of both agents in the vitreous cavity was found to be significantly less than the 4- to 6-week treatment interval typically used in clinical practice. However, the physiologic effects of these agents may remain active after they are no longer detectable by PET imaging. Klettner and Roider have demonstrated that VEGF suppression lasted longer than the persistence of VEGF inhibitors in porcine RPE cell cultures treated with bevacizumab and ranibizumab (Alexa Klettner, et al. Invest Ophthalmol Vis Sci. 2008 49:4523-4527).

The half-lives for ranibizumab and bevacizumab in this study (2.8 and 4.2 days, respectively) were found to compare favorably with previously reported findings using immunoassay techniques. Using a rabbit model, halflives in the vitreous cavity were found to be 3.2 days for ranibizumab and 4.32 days for bevacizumab (Bakri S J, et al. Ophthalmology. 2007 114:855-859; Bakri S J, et al. Ophthalmology. 2007 114:2179-2182). The half-life of rituximab, a 145-kDa agent similar in size to bevacizumab, was found to be 4.7 days (Kim H, et al. Exp Eye Res. 2006 82:760-762). In primates after bilateral intravitreal injection (0.5 mg), half-lives were found to be 3.2 in ranibizumab and 5.6 days in a 148-kDa anti-VEGF agent (rhuMab) that is similar in size to bevacizumab (Gaudreault J, et al. Invest Ophthalmol Vis Sci. 2005 46:726-733). Findings in the disclosed model indicate the presence of a two-compartment pharmacokinetic decay model similar to that previously described (Alexa Klettner, et al. Invest Ophthalmol Vis Sci. 2008 49:4523-4527), with an initial rapid distribution phase to day 5, followed by a subsequent slower elimination phase.

The number of animals studied per agent was limited to six each day because of the large amount of time necessary to prepare and image each rabbit. Despite this, serial measurements were obtained at multiple time points (six or seven) for each animal. Previous pharmacokinetic studies with immunoassay methods have used larger numbers of animals to determine intravitreal anti-VEGF agent levels. However, each time point in these studies represented a separate animal, and between one and four measurements were obtained at each time point (Bakri S J, et al. Ophthalmology. 2007 114:855-859; Bakri S J, et al. Ophthalmology. 2007 114:2179-2182; Kim H, et al. Exp Eye Res. 2006 82:760-762; Gaudreault J, et al. Invest Ophthalmol Vis Sci. 2005 46:726-733).

In conclusion, PET/CT imaging of intravitreally placed I-124 ranibizumab and I-124 bevacizumab revealed no evidence of significant escape from the vitreous cavity into the central nervous system or elsewhere in a rabbit model. In addition, the intravitreal pharmacokinetic properties of these agents appear to be consistent with those described in previous reports using different techniques. The described methodology offers a unique approach for studying the anatomic and pharmacokinetic properties of novel intravitreally placed therapeutic agents with all measurements in one animal.

Example 2

Pharmacokinetic Properties of Intravitreal I-124-Aflibercept in a Rabbit Model Using PET/CT Integrated PET/CT was used to image intravitreally placed I-124 aflibercept in rabbit eyes. Whether aflibercept remains within the vitreous cavity after intravitreal placement was evaluated. Its pharmacokinetic properties were also evaluated by sequential ocular imaging of each subject.

Materials and Methods

Radiolabeling of aflibercept with I-124 (IBA Molecular, Dulles, Va., USA) was performed with a modified Iodogen method previously described (Zou P, et al. World Journal of Surgical Oncology. 2010 8:65). The radiochemical purity of I-124 labeled aflibercept was 96%. Four Dutch-belted rabbits (Robinson Services Inc, Mocksville, N.C., USA) weighing 1.3-1.7 kg were used for this study. All experimental protocols were approved, and the procedures followed were in accordance with the ethical standards of The Institutional Animal Care and Use Committee (IACUC) at The Ohio State University. All treatments were conducted in agreement with the ARVO Statement for the Use of Animals in Ophthalmic and Vision Research. The rabbits were anesthetized with intramuscularly-placed 0.1-0.2 mL xylazine (5 mg/mL) and 1.5-2.0 mL ketamine hydrochloride (100 mg/mL). In each rabbit, intravitreal injection consisting of 2.0 mg/0.05 mL I-124-aflibercept was performed 1 mm posterior to the limbus of the left eye.

The rabbit subjects were then imaged with the microPET/CT (Inveon, Siemens Preclinical, Knoxville, Tenn., USA) using a method previously described (Christoforidis J B, et al. Invest Ophthalmol Vis Sci. 2011 52:5899-5903). The rabbits were imaged on days 0, 2, 5, 7, 14, 21, 28 and 35. A phantom containing 2.0 mg in 0.5 mL I-124 aflibercept in a polyethylene microcentrifuge tube was imaged at each time point. The range of radioactive emission from the vitreous cavity was set at 0-50% in order to eliminate noise and to provide a consistent range of emission for all the figures. One week after completion of the study, the rabbits were adopted out as pets. The radioactive units were corrected to account for I-124 radioactive decay which has a physical half-life of 4.18 days. Clearance curves were then formulated with the resulting measurements and the intravitreal half-life for each subject was calculated using a formula to describe first order kinetics below:

$$T_{1/2} = (T \times \log 2)/(\log [\text{Drug}]_b/[\text{Drug}]_e)$$

where $T_{1/2}$ is the half-life, T is the elapsed time, $[\text{Drug}]_b$=Beginning Amount, and $[\text{Drug}]_e$=Ending Amount.

Results

Anatomic Properties

Figure 5:
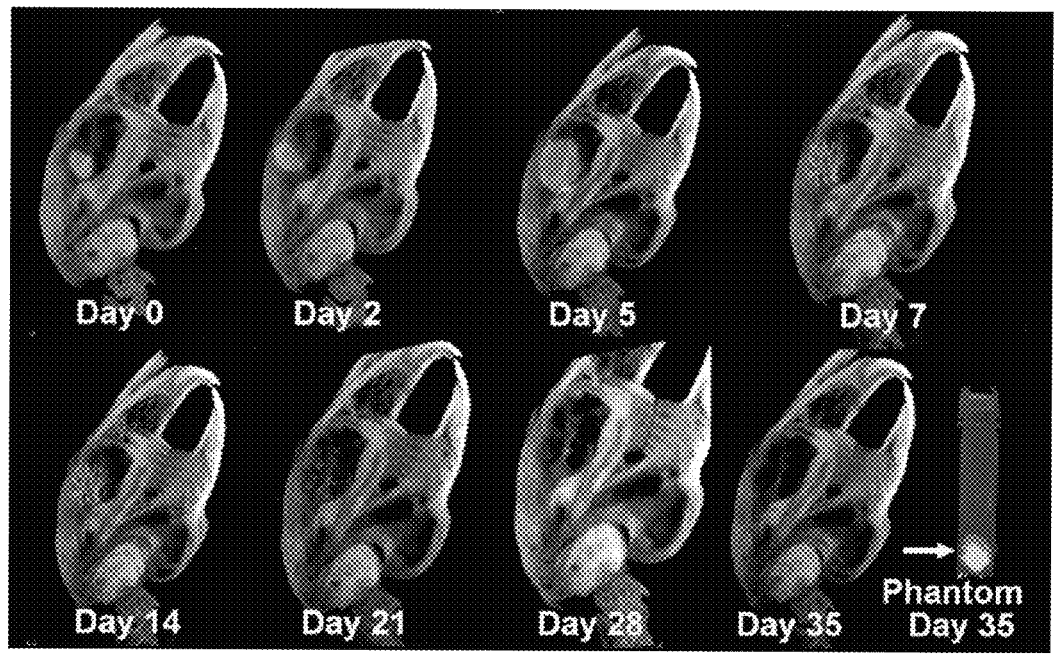
FIG. 5 is an image montage illustrating clearance patterns of I-124 aflibercept within the vitreous cavity in a rabbit model. The agent is still discernible on day 21, detectable on day 28 and compatible with background noise on day 35. A phantom containing I-124 aflibercept in a microcentrifuge tube is easily discerned on day 35 (arrow) indicating that the lack of positron emission in the vitreous cavity is due to aflibercept clearance rather than I-124 decay. Range of acquisition of radioactive emission is 0 to 50%.
Figure 6:
FIG. 6 is a PET/CT image demonstrating sequestration of I-124 in the thyroid gland on day 14 (arrow). The range of radioactive emission acquisition is set between 5 and 20% to allow detection of lower levels.

I-124 aflibercept was only detectable in the vitreous and thyroid for the duration of the study in the four rabbits. There were no untoward adverse effects in any of the subjects including endophthalmitis, uveitis, vitreous hemorrhage or cataract due to lens incarceration of the needle tip. The image montage illustrates serial images for I-124 aflibercept (FIG. 5). Aflibercept was visible until day 21 and detectable until day 28. Any further detection beyond day 28 was indistinguishable from background noise. Radioactivity emissions (Bq/mL) from the vitreous cavity of each rabbit are shown in Table 1. Radioactivity measurements less than 30 Bq/mL are compatible with background noise. I-124 was sequestered and visible in the thyroid gland at lower emission thresholds than in the vitreous cavity (FIG. 6). In all four subjects, I-124 in the thyroid was visible from day 0 with peaked levels on day 2 and detectable until day 21.

Pharmacokinetic Properties

Figure 7:
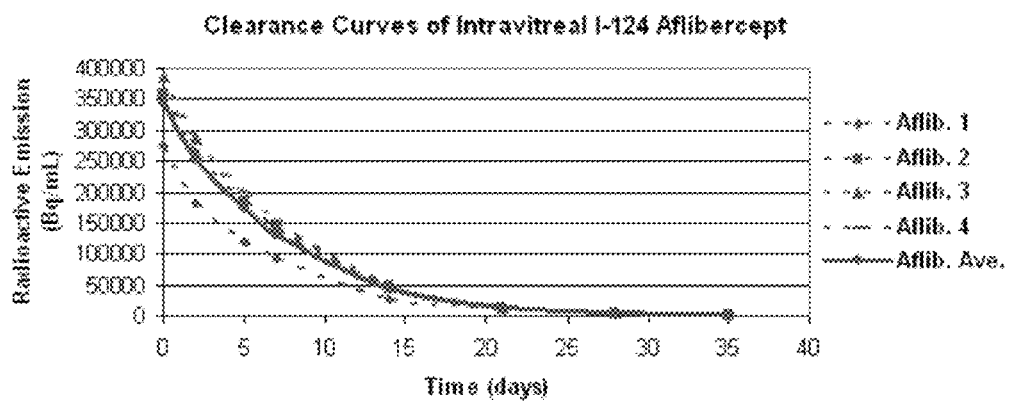
FIG. 7 is a graph demonstrating intravitreal clearance curves of I-124 labeled aflibercept. Curves with dashes represent radioactive emissions of each individual subject. The solid curve represents the average radioactive emission. The curves are consistent between the subjects and I-124 aflibercept is detectable until day 28.

The individual clearance curves were concordant among the four subjects (FIG. 7) and demonstrated a one-compartment pharmacokinetic model. The phantom containing I-124 aflibercept was easily visible on day 35 (FIG. 5) indicating that the lowered radioactivity emission within the vitreous cavity was due to egress of the agent from the vitreous cavity rather than radioactive decay. The average intravitreal half-life was calculated to be 4.58 (±0.074) days consistent with one preliminary report using immunoassay methods in a rabbit model (Struble C, et al. Acta Ophthalmologica 2008 s243: 0).

Discussion

In this study, intravitreally placed I-124 aflibercept was imaged with PET/CT. Aflibercept remained within the vitreous cavity or in the thyroid gland throughout the study. Integrated PET/CT imaging allows the visualization of a radiolabeled agent in a direct and non-invasive manner, to follow the same subject over time, and to determine the pharmacokinetic properties of the intravitreally placed agent. Although only four rabbits were studied, serial measurements were obtained at 8 time points for each subject. Thus, the number of total measurements obtained by PET/

CT compares favorably with those of intravitreal pharmacokinetic studies using immunoassay detection methods.

After I-124 aflibercept diffuses into the blood stream, I-124 becomes decoupled from the agent substrate and is sequestered by the thyroid. I-124 levels in the blood are below PET/CT detection thresholds but levels in the thyroid were found to be low and consistent with background noise after day 21.

Aflibercept was detectable within the vitreous until day 28 in all four subjects while the phantom containing I-124 aflibercept was visible at day 35. The duration of aflibercept in the al. Angiogenesis. 2012 15:171-185) and may still provide significant VEGF blockade after it is no longer detectable by PET imaging. Furthermore, there may be other pathways that continue to suppress VEGF after VEGF inhibition agents are no longer detectable such as VEGF receptor inhibitory feedback mechanisms (Klettner A, et al. Invest Ophthalmol vitreous was less than the 8 weeks between treatments recommended by VIEW 1 and VIEW 2 and typically used for this agent in clinical practice (Nguyen Q D, et al. Investig Ophthalmol Vis Sci. 2011 52: 3073; Schmidt-Erfurth U, et al. Investig Ophthalmol Vis Sci. 2011 52: 1650). However, aflibercept has a binding affinity to VEGF-$A_{165}$ that is approximately 100 times that of bevacizumab and 70 times that of ranibizumab (Papadopoulos N, et Vis Sci. 2008 49:4523-27). Despite the longer half-life and greater binding affinity of aflibercept, the rate of adverse systemic events and safety profile was comparable to the ranibizumab treatment arm in VIEW 1 and VIEW 2 (Nguyen Q D, et al. Investig Ophthalmol Vis Sci. 2011 52: 3073; Schmidt-Erfurth U, et al. Investig Ophthalmol Vis Sci. 2011 52: 1650).

In conclusion, intravitreally placed I-124 aflibercept was only detectable in the vitreous and thyroid for the duration of the study in the four rabbits by PET/CT imaging. The pharmacokinetic properties of the intravitreal agent were determined from the radioactive emission and are consistent with those in a previous report in a rabbit model using different techniques. Sequential PET/CT imaging of the same subject over time offers a unique methodology for examining the anatomic and pharmacokinetic properties of therapeutic agents in the vitreous cavity.

Example 3

Anatomic and Pharmacokinetic Properties of Intravitreal Bevacizumab and Ranibizumab after Vitrectomy and Lensectomy PET/CT was used to image intravitreally placed I-124 radiolabeled bevacizumab and ranibizumab in a rabbit model following vitrectomy or lensectomy. Whether or not intravitreal anti-VEGF agents placed after vitrectomy or lensectomy remain within the vitreous cavity was determined. The pharmacokinetic properties of these two agents in eyes after vitrectomy and lensectomy were also evaluated and compare with non-operated eyes.

Materials and Methods

Bevacizumab and ranibizumab were radiolabeled with I-124 (IBA Molecular, Dulles, Va., USA) using a modified Iodogen method previously described (Zou P, et al. World Journal of Surgical Oncology 2010 8:65). Radiochemical purity of I-124 labeled bevacizumab and I-124 ranibizumab was found to be 95% and 98% respectively.

Eighteen male Dutch-belted rabbits (Myrtle's Rabbitry Inc, Thompsons Station, Tenn., USA) weighing 1.5-1.8 kg were used for this study. All experimental protocols were approved, and the procedures followed were in accordance with the ethical standards of the Institutional Animal Care and Use Committee (IACUC) at The Ohio State University. All treatments were conducted in agreement with the ARVO Statement for the Use of Animals in Ophthalmic and Vision Research. Six rabbits underwent pars plana vitrectomy, 6 rabbits underwent pars plana lensectomy and 6 rabbits served as non-surgical controls. The rabbits were anesthetized with 0.1-0.2 ml xylazine (5 mg/ml) and 1.5-2.0 ml ketamine hydrochloride (100 mg/ml) placed intramuscularly. An Alcon Accurus vitrector (Alcon Laboratories, Fort Worth, Tex., USA) was used, and all of the procedures were performed on the left eye by one surgeon (JC). After the surgeries, the vitrectomized and lensectomized eyes were treated with topical tobradex ointment twice a day for 3 and 7 days respectively. The rabbits were monitored daily and by day 7 all of the operated eyes were absolutely quiet and the sclerotomy sites were white and closed. Twelve days following the surgical procedures, the operated eye of each anesthetized rabbit underwent an intravitreal injection with a 32 gauge needle 1 mm posterior to the limbus consisting of 0.05 ml containing 0.5 mg/0.05 ml I-124 labeled ranibizumab or 1.25 mg/0.05 ml I-124 labeled bevacizumab.

The anesthetized rabbits were then lightly secured to the scanner bed with elastic socks or gauze for imaging. The animals were imaged for 10 minutes in the microPET/CT (Inveon, Siemens Preclinical, Knoxyille, Tenn., USA), followed by an attenuation scan of 15 minutes. The microPET scans each resulted in a reconstructed volume with an effective pixel size of 0.78 mm, while the microCT had an effective pixel size of 0.099 mm. The scans were performed on days 0, 2, 5, 7 and then weekly until 1 week after the radiolabeled agent was undetectable. This occurred on day 21 for ranibizumab and day 28 for bevacizumab in the post-surgical eyes and on day 28 and day 35 respectively in the non-surgical eyes. In order to eliminate noise and provide a consistent range of emission, the range of radioactive emission was set at 10-75% for all of the figures. Euthanasia was carried out after the last imaging session by intravenous injection of 3 ml of saturated KCl.

The radioactive units were becquerels/ml and these were modified with a correction factor to account for radioactive decay of I-124 which has a physical half-life of 4.18 days. The radioactive measurements were used to formulate the retention curves and to calculate the intravitreal clearance half-lives for each agent using the following formula for first order kinetics:

$$T_{1/2} = (T \times \log 2)/(\log [\text{Drug}]_b/[\text{Drug}]_e)$$

where $T_{1/2}$ is the half-life, T is the elapsed time, $[\text{Drug}]_b$=Beginning Amount, and $[\text{Drug}]_e$=Ending Amount.

Statistical analysis was performed using a general linear model to fit and compare the difference in clearance half life between surgery groups and the control group. Dunnett-Hsu's method for multiple comparisons was used to adjust for multiple hypothesis tests. All analyses were performed using SAS/STAT software, Version 9.2 (SAS Institute Inc., Cary, N.C., USA) under Windows XP system.

Results

Escape from the Vitreous Cavity.

Figure 8:
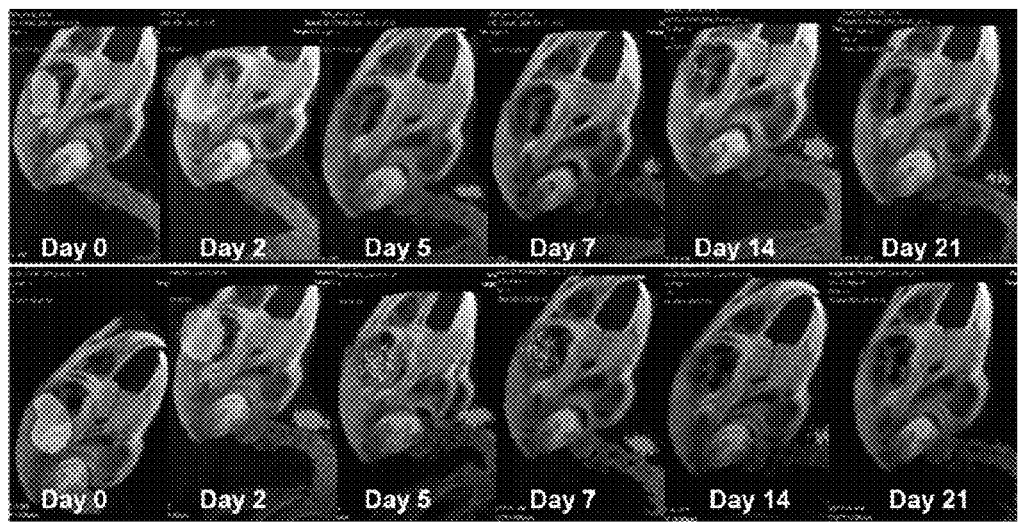
FIG. 8 are image montages illustrating clearance patterns of I-124 bevacizumab (top) and I-124 ranibizumab (bottom) within the vitreous cavity after pars plana vitrectomy in a rabbit model. Note the I-124 accumulation in the thyroid gland. Range of acquisition of radioactive emission is 10 to 75%.
Figure 9:
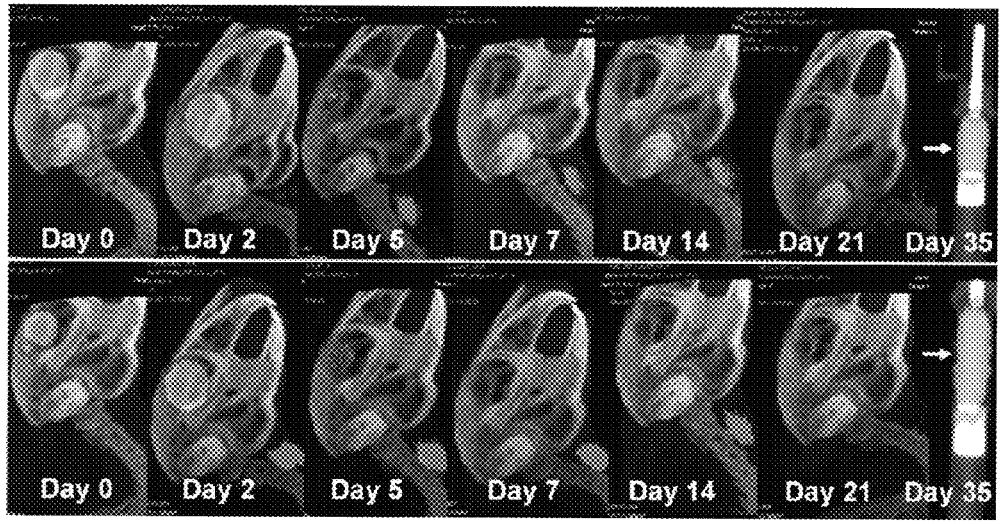
FIG. 9 are image montages illustrating clearance patterns of I-124 bevacizumab (top) and I-124 ranibizumab (bottom) within the vitreous cavity after pars plana lensectomy in a rabbit model. Note the I-124 accumulation in the thyroid gland. A phantom containing I-124 bevacizumab (top) and I-124 ranibizumab (bottom) in a tuberculin syringe is easily discerned on day 35 (arrow). Range of acquisition of radioactive emission is 10 to 75%.

In all eighteen rabbits I-124 bevacizumab and I-124 ranibizumab were not detectable outside the vitreous cavity and the thyroid for the length of the study following intravitreal injection. None of the eyes developed evidence of endophthalmitis, uveitis or other adverse events during the study. The 2 montages illustrate sequential post-operative images for each agent over time after vitrectomy (FIG. 8) and after lensectomy (FIG. 9).

Figure 10:
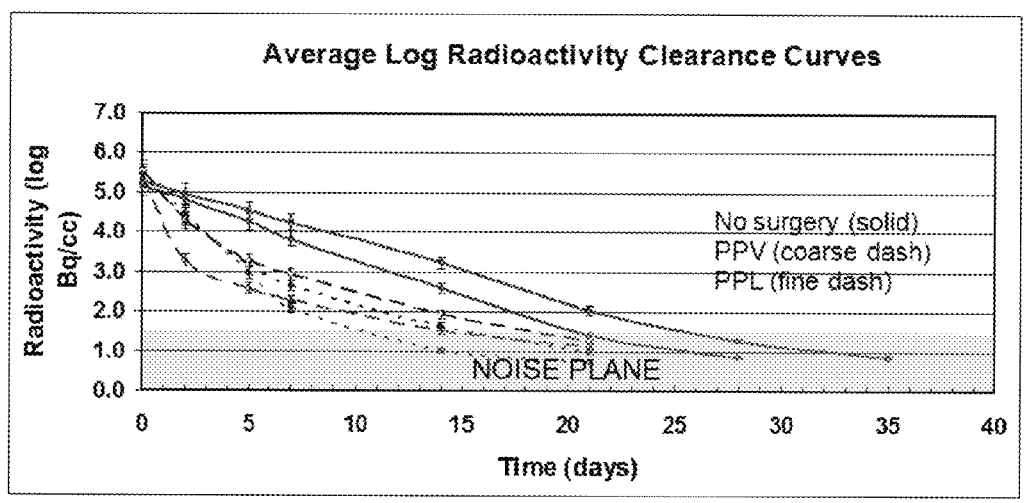
FIG. 10 is a graph demonstrating average log clearance curves for I-124-labeled bevacizumab and ranibizumab in unoperated eyes (solid), after vitrectomy (coarse dashes) and after lensectomy (fine dashes). The units are corrected for I-124 radioactive decay. The noise plane indicates the level of background noise (<30 Bq/ml).

Intravitreal levels of radioactivity (Bq/ml) are listed for each rabbit in Table 3. Radioactivity levels below 30 Bq/ml were considered compatible with background noise. I-124 counts were highly elevated throughout the study in one vitrectomized eye injected with I-124 bevacizumab (subject 2) presumably due to incarceration of I-124 bevacizumab within the lens, and the data from this subject were not used in the PK calculations. By graphic extrapolation of I-124 levels to the noise plane at 30 Bq/ml, average I-124 bevacizumab was detectable in the vitreous until day 26 in unoperated eyes, day 22 after vitrectomy and day 19 after lensectomy (FIG. 10). Average I-124 ranibizumab was detectable in the vitreous until day 21 in unoperated eyes, 19 days after vitrectomy and 13 days after lensectomy (FIG. 10). Phantoms of I-124 ranibizumab and I-124 bevacizumab in tuberculin syringes were clearly visible on day 35 indicating that the lack of positron emission in the vitreous cavity was due to agent clearance rather than I-124 decay (FIG. 9).

TABLE 3

Intravitreal radioactivity levels (Bq/ml)

| Day | Bev. 1 | Bev. 2 | Bev. 3 | Ran. 1 | Ran. 2 | Ran. 3 |
| --- | --- | --- | --- | --- | --- | --- |
| 0 | 175370.0 | 205250.0 | 178970.0 | 167730.0 | 116000.0 | 164540.0 |
| 2 | 84861.5 | 106740.0 | 89862.3 | 89780.3 | 50111.7 | 69510.8 |
| 5 | 31247.2 | 38312.8 | 33722.5 | 21029.2 | 14030.5 | 19604.7 |
| 7 | 15523.8 | 19824.4 | 17006.6 | 5933.5 | 5946.1 | 8350.8 |
| 14 | 1549.1 | 1929.9 | 1695.3 | 470.6 | 275.7 | 454.5 |
| 21 | 174.5 | 44.3 | 161.4 | 31.6 | 16.7 | 31.1 |
| 28 | 17.2 | 23.8 | 15.9 | 4.9 | 8.2 | 9.1 |
| 35 | 7.6 | 5.1 | 9.1 | | | |

| Day | Bev. 1-PPV | Bev. 2-PPV | Bev. 3-PPV | Ran. 1-PPV | Ran. 2-PPV | Ran. 3-PPV |
| --- | --- | --- | --- | --- | --- | --- |
| 0 | 327500.0 | 318600.0 | 360480.0 | 278150.0 | 234510.0 | 225600 |
| 2 | 22463.8 | 107000.0 | 16220.1 | 4972.4 | 2186.5 | 663.4 |
| 5 | 2186.6 | 27782.9 | 1663.8 | 1322.1 | 281.0 | 143.8 |
| 7 | 1043.9 | 16415.4 | 707.2 | 650.9 | 169.7 | 67.0 |
| 14 | 108.0 | 3342.2 | 69.8 | 60.1 | 35.8 | 16.9 |
| 21 | 21.8 | 630.4 | 16.2 | 9.6 | 15.7 | 7.1 |
| 28 | 8.6 | 110.2 | 5.9 | | | |
| 35 | | 33.3 | | | | |

| Day | Bev. 1-PPL | Bev. 2-PPL | Bev. 3-PPL | Ran. 1-PPL | Ran. 2-PPL | Ran. 3-PPL |
| --- | --- | --- | --- | --- | --- | --- |
| 0 | 332020.0 | 365280.0 | 346410.0 | 309570.0 | 245630.0 | 272970.0 |
| 2 | 30857.3 | 9899.4 | 42150.5 | 48136.8 | 32017.1 | 14947.9 |
| 5 | 1760.8 | 698.1 | 2357.7 | 2456.4 | 1835.3 | 168.7 |
| 7 | 477.9 | 321.7 | 596.8 | 169.0 | 286.8 | 38.8 |
| 14 | 31.5 | 39.9 | 71.0 | 11.4 | 10.0 | 9.3 |
| 21 | 6.0 | 10.0 | 15.3 | 4.6 | 5.1 | 7.1 |

Accumulation of I-124 in the thyroid gland was detectable at lower emission thresholds in the non-operated subjects and was only visible until day 14 in 5/6 subjects. By comparison, thyroid I-124 levels were greatly elevated and clearly visible on day 21 in all post-surgical subjects (Table 4 and FIGS. 8 and 9).

TABLE 4

Thyroid radioactivity levels (Bq/ml)

| Day | Bev. 1-Control | Bev. 2-Control | Bev. 3-Control | Ran. 1-Control | Ran. 2-Control | Ran. 3-Control |
| --- | --- | --- | --- | --- | --- | --- |
| 2 | 429.4 | 490.6 | 351.3 | 475.0 | 410.0 | 464.9 |
| 5 | 311.4 | 388.5 | 272.8 | 321.0 | 416.0 | 367.6 |
| 7 | 224.0 | 323.4 | 217.3 | 207.1 | 297.1 | 294.4 |
| 14 | 77.2 | 113.8 | 71.1 | 43.5 | 71.8 | 59.1 |
| 21 | | 33.6 | | | | |

| Day | Bev. 1-PPV | Bev. 2-PPV | Bev. 3-PPV | Ran. 1-PPV | Ran. 2-PPV | Ran. 3-PPV |
| --- | --- | --- | --- | --- | --- | --- |
| 2 | 2267.8 | 1176.5 | 2490.6 | 2225.4 | 2406.3 | 1144.7 |
| 5 | 2268.2 | 1618.5 | 2799.8 | 1424.6 | 1278.0 | 656.7 |
| 7 | 1463.8 | 940.2 | 2084.6 | 852.2 | 792.6 | 379.4 |
| 14 | 430.4 | 235.0 | 605.3 | 152.4 | 162.2 | 52.0 |
| 21 | 89.2 | 63.0 | 91.3 | 27.9 | 35.2 | 8.7 |
| 28 | 21.3 | 17.3 | 32.4 | 10.7 | | 6.1 |
| 35 | | 10.9 | | | | |

| Day | Bev. 1-PPL | Bev. 2-PPL | Bev. 3-PPL | Ran. 1-PPL | Ran. 2-PPL | Ran. 3-PPL |
| --- | --- | --- | --- | --- | --- | --- |
| 2 | 1879.2 | 3095.4 | 3306.2 | 4453.2 | 10001.2 | 4248.3 |
| 5 | 1242.4 | 2183.1 | 2599.3 | 2355.4 | 4965.8 | 1804.7 |
| 7 | 890.7 | 1400.4 | 2039.7 | 1444.5 | 2879.3 | 1077.2 |
| 14 | 332.7 | 359.0 | 551.7 | 251.6 | 548.7 | 219.5 |
| 21 | 70.1 | 79.9 | 145.8 | 82.0 | 108.1 | 48.7 |

Pharmacokinetic Properties

The resultant clearance patterns were consistent within each group of subjects (FIG. 10). For each subgroup, the clearance appeared to fit a 2 phase curve with an initial rapid distribution phase until day 5 followed by a slower elimination phase. The average clearance half-lives with standard error and confidence intervals for bevacizumab and ranibizumab after correction for radioactive decay were found to be 4.22±0.07 (4.04, 4.40) days and 2.81±0.05 (2.68, 2.93) days respectively in unoperated eyes, 2.30±0.09 (2.07, 2.52) ($p<0.0001$) and 2.13±0.05 (2.01, 2.25) ($p<0.0001$) after vitrectomy and 2.08±0.07 (1.90, 2.27) ($p=0.0001$) and 1.79±0.05 (1.66, 2.91) ($p<0.0001$) days after lensectomy. In comparison to vitrectomy, lensectomy further reduced retention of bevacizumab ($p=0.007$) and ranibizumab ($p=0.230$).

Discussion

The clearance half-lives of intravitreally placed I-124 bevacizumab and I-124 ranibizumab were found to be significantly reduced following vitrectomy and lensectomy for both agents compared to non-surgical control eyes. The clearance half-lives were longer for bevacizumab than ranibizumab in all three study groups. The increased intravitreal clearance rates of bevacizumab and ranibizumab following vitrectomy and lensectomy are consistent with the findings of other intravitreal agents reported in previous studies using different methodologies in a rabbit model. Triamcinolone was shown to disappear more rapidly in eyes that underwent combined vitrectomy and lensectomy (6.5 days) and vitrectomy only (16.8 days) compared to unoperated rabbit eyes (41 days) (Schindler R H, et al. Am J Ophthalmol 1982 93(4):415-417). In other reports, the intravitreal agent clearances for normal phakic eyes and vitrectomized-lensectomized in rabbit model eyes were found to be 9.1 and 1.4 days respectively for amphoterecin B (Doft B H, et al. Ophthalmology 1985 92(11):1601-1605), 2.2 hours and 1 hour for ciprofloxacin (Pearson P A, et al. Retina 1993 13(4):326-330), 25.5 and 7.0 hours for amikacin (Mandell B A, et al. Am J Ophthalmol 1993 115(6):770-774), 25.1 hours to 9.0 hours for vancomycin (Aguilar H E, et al. Retina. 1995 15(5):428-432) and 13.8 and 4.7 hours for ceftazidime (Shaarawy A, et al. Retina. 1995 15(5):433-438).

The significant intravitreal clearance half-life reduction for both anti-VEGF agents after vitrectomy compared to non-surgical controls was surprising since the vitrectomized rabbits retained their native lenses. Vitrectomy by itself creates a vitreous with lower viscosity that allows for increased convection that may help to disperse bevacizumab and ranibizumab faster than in non-vitrectomized eyes (Gisladottir S, et al. Graefes Arch Clin Exp Ophthalmol. 2009 247: 1677-1684). However, it is unclear whether the route of escape is primarily anterior through the trabecular meshwork or posterior through the retina and choroid. The significant decrease in retention time after vitrectomy in the presence of an intact lens would indicate a more likely posterior outflow mechanism.

The addition of lensectomy further reduced retention that was significant for bevacizumab ($p=0.007$) but not significant for ranibizumab ($p=0.230$). Although the cause for this difference between the two agents is unclear, the decreased retention time after lensectomy may indicate the addition of an anterior escape route despite preservation of the anterior capsule. Preservation of the anterior capsule has been shown to slow the clearance rate of intravitreal agents and more accurately simulates a phakic model in a rabbit (Pflugfelder S C, et al. Arch Ophthalmol 1987 105: 831-837). Since the vitreous and the posterior lens capsule are usually preserved during cataract surgery, it seems plausible that the clearance half-life of intravitreal anti-VEGF therapy would not be greatly affected in pseudophakic patients.

A previously vitrectomized eye would be expected to be less responsive to standard intravitreal treatment intervals due to more rapid clearance of the agent from the eye. A retrospective study showed reduced efficacy of intravitreal bevacizumab for diabetic macular edema following previous pars plana vitrectomy by examining foveal thickness by OCT and visual acuity (Yanyali A, et al. Am J Ophthalmol. 2007 144:124-126). The use of an intravitreal device with sustained-release of drug would be a plausible solution in previously vitrectomized or aphakic eyes. In the CHAMPLAIN Study, intravitreal placement of a single dexamethasone implant (Ozurdex, Allergan Inc., Irvine, Calif.) for the treatment of diabetic macular edema in previously vitrectomized eyes resulted in improvement of visual acuity and central retinal thickness that remained significantly improved throughout the 26-week study (Boyer D S, et al. Retina. 2011 31:915-923).

The presence of posterior vitreous detachment (PVD) is often seen in patients that are treated with anti-VEGF intravitreal therapy. The increased vitreous liquefaction present in a PVD can partially simulate the increased clearance rates of intravitreally placed agents seen with vitrectomy. Bevacizumab has been shown to be absorbed more quickly through the retina following microplasmin-induced PVD compared to non-treated eyes in a rabbit model (Goldenberg D T, et al. Retina. 2011 31:393-400). Gad Elkareem et al. demonstrated higher differential fluorescein diffusion rates in both plasmin and microplasmin compared to saline treated vitreous cavities (Gad Elkareem A M, et al. Curr Eye Res. 2010 35:235-241).

There was no evidence of bevacizumab and ranibizumab escape from the vitreous cavity into the central nervous system or elsewhere in any of the subjects during the length of the study. Once the anti-VEGF agent is absorbed into the blood stream, I-124 decouples from its substrate and is sequestered in the thyroid gland. Iodine-124 was detected in the thyroid in all groups, most prominently in the post-surgical rabbits. It is unlikely that there was agent escape through the surgical sclerotomy sites. 23 gauge (0.57 mm) sclerotomy wounds are expected to be completely healed 12 days after the intraocular procedures. Previously Hikichi et al. demonstrated that 3.2 mm sclerotomy wounds in a rabbit model were completely healed both histologically and by ultrasound biomicroscopy by post-operative day 7 (Hikichi T, et al. Graefes Arch Clin Exp Ophthalmol. 1998 236(10): 775-778). Measurement of hematogenous agent escape is below PET/CT resolution thresholds and cannot be excluded based on the disclosed findings.

The advantage of integrated PET/CT imaging compared to immunoassay methods for studying the pharmacokinetic properties of intravitreally placed agents lies in its ability to directly and non-invasively visualize the labeled agent and to serially follow the same subject over time. The use of this method is particularly advantageous in studying post-surgical subjects since the variables of performing a larger number of surgeries for multiple time points are minimized. Although the number of rabbits studied per treatment group was small, serial measurements were obtained at 6 to 8 time points for each subject. Thus, the number of total measurements obtained by PET/CT compares favorably with those of intravitreal pharmacokinetic studies using immunoassay methods.

In conclusion, PET/CT imaging of intravitreally placed I-124 ranibizumab and I-124 bevacizumab revealed significantly faster clearance rates for both agents after vitrectomy and lensectomy compared to placebo non-surgical controls in a rabbit model. Based on these findings, a more frequent treatment regimen of anti-VEGF therapy may be considered in non-responding treated patients who have undergone previous vitrectomy or who are aphakic. The described methodology offer a unique approach for studying the anatomic and pharmacokinetic properties of intravitreally-placed therapeutic agents in normal and post-surgical subjects.

Example 4

The Subconjunctival Bleb that Forms at the Injection Site after Intravitreal Injection is Drug, not Vitreous PET/CT imaging was utilized to examine the presence of subconjunctival bleb following intravitreal injection with I-124 labeled anti-VEGF agents in a rabbit model.

Figure 11:
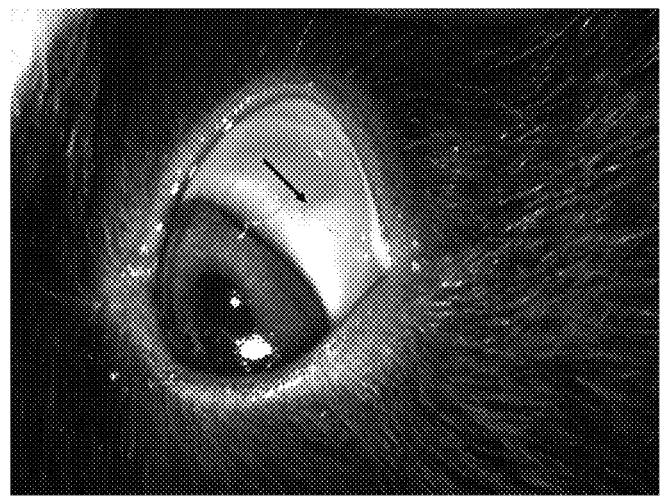
FIG. 11 is an external image of the left eye in a rabbit model demonstrating a subconjunctival bleb following intravitreal injection with I-124 aflibercept (arrow).
Figure 12:
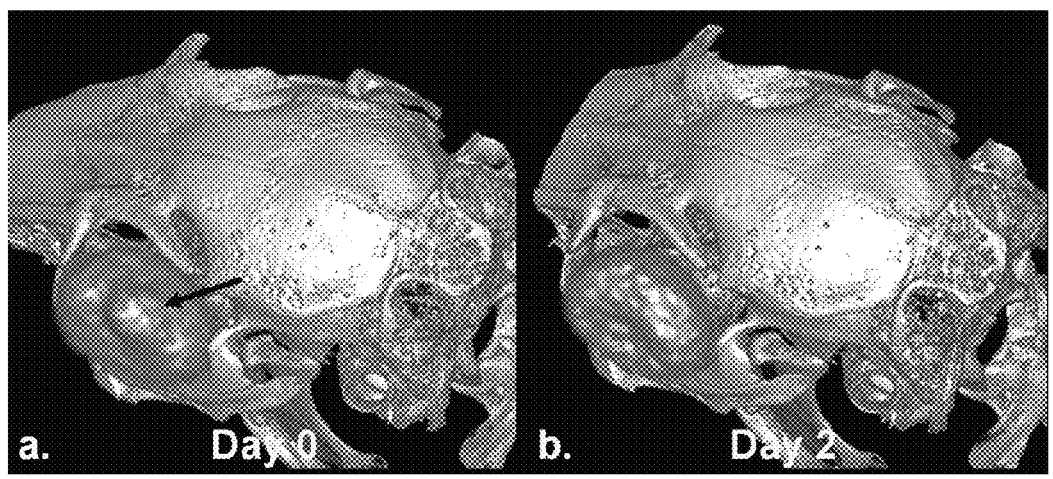
FIG. 12 is a PET/CT image of the rabbit in FIG. 11 immediately following intravitreal injection with I-124-aflibercept. The bleb containing I-124-aflibercept is visible extending from the intravitreally placed drug in the image (FIG. 12A, arrow). At day 2, the bleb has disappeared completely (FIG. 12B)

PET/CT was used to examine the eyes of 29 Dutch-belted rabbits after intravitreally placed I-124 labeled anti-VEGF agents. Nine anesthetized rabbits underwent intravitreal injection with I-124 bevacizumab (Roche, Basel, Switzerland), with I-124 ranibizumab (Roche, Basel, Switzerland) and with I-124 aflibercept (Regeneron, Tarrytown, N.Y., USA). The injections consisted of 0.05 ml containing standard clinical doses of each agent placed 1 mm posterior to the limbus of the left eye in each rabbit using 32 gauge needles. A cotton swab applicator was used to prevent reflux and tunneling incisions were not performed. Immediately following injection, each subject was imaged with micro PET/CT (Inveon, Siemens Preclinical, Knoxyille, Tenn., USA). A bleb extending from the main body of the drug at the injection site was visible in 14/29 subjects. (5/9 bevacizumab, 3/9 ranibizumab and 6/11 aflibercept, FIG. 11). The subconjunctival bleb at the injection site was clearly visible by PET/CT (FIG. 12A) and had disappeared at day 2 (FIG. 12B).

The hypothesis that refluxed material within the subconjunctival bleb formed following intravitreal injection may be drug was previously proposed (Cortez R T, et al. Arch Ophthalmol 2010 129: 884-7). These data further support this hypothesis as PET/CT imaging demonstrates the radiolabeled drug within the bleb extending directly from the labeled drug in the vitreous cavity. To reduce the formation of a subconjunctival bleb after intravitreal injection, various techniques such as the use of tunneled incision, vitreous softening with Homan cuff, pre-procedure paracentesis for intraocular pressure reduction, smaller gauge needles and placement of a cotton swab applicator at the injection site to prevent reflux may be utilized. The presence of drug rather than vitreous in the subconjunctival space following intravitreal injection points to the delivery of a smaller than intended intravitreal dosage but also reduces the possibility of complications that may be associated with vitreous loss.

A number of embodiments of the invention have been described. Nevertheless, it will be understood that various modifications may be made without departing from the spirit and scope of the invention. Accordingly, other embodiments are within the scope of the following claims.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for evaluating a pharmacokinetic property of an intravitreally placed anti-vascular endothelial growth factor (VEGF) agent, comprising
    a) administering a composition comprising the anti-VEGF agent Bevacizumab or Ranibizumab radiolabeled with iodine-124($^{124}$I) into the vitreous cavity of the eye of a subject,
    b) serially imaging the eye of the subject to detect positron emission levels in the vitreous cavity of the eye by positron emission tomography-computed tomography (PET-CT), and
    c) calculating a pharmacokinetic property of the ophthalmic agent from the positron emission levels measured in step b), wherein the pharmacokinetic property is selected from the group consisting of clearance pattern and intravitreal half-life.

2. The method of claim 1, wherein the subject has been diagnosed with age-related macular degeneration (AMD).

* * * * *